(12) United States Patent
Stamper et al.

(10) Patent No.: US 7,699,882 B2
(45) Date of Patent: Apr. 20, 2010

(54) APPARATUS AND METHOD FOR SURGICAL BYPASS OF AQUEOUS HUMOR

(75) Inventors: Robert Stamper, Berkeley, CA (US); Stanley R. Conston, San Carlos, CA (US); Ronald K. Yamamoto, San Francisco, CA (US)

(73) Assignee: iScience Interventional Corporation, Menlo Park, CA (US)

( * ) Notice: Subject to any disclaimer, the term of this patent is extended or adjusted under 35 U.S.C. 154(b) by 1177 days.

(21) Appl. No.: 10/528,276

(22) PCT Filed: Sep. 17, 2003

(86) PCT No.: PCT/US03/29488
§ 371 (c)(1),
(2), (4) Date: Sep. 8, 2005

(87) PCT Pub. No.: WO2004/026347
PCT Pub. Date: Apr. 1, 2004

(65) Prior Publication Data
US 2006/0155300 A1    Jul. 13, 2006

Related U.S. Application Data

(60) Provisional application No. 60/411,668, filed on Sep. 17, 2002.

(51) Int. Cl.
*A61F 2/06* (2006.01)
*A61F 9/00* (2006.01)

(52) U.S. Cl. .................................. 623/1.11

(58) Field of Classification Search ............. 623/1.11, 623/1.12; 606/4, 5, 6; 604/8, 9, 10, 27, 28
See application file for complete search history.

(56) References Cited

U.S. PATENT DOCUMENTS

| 4,428,746 A | 1/1984 | Mendez |
| 4,554,918 A | 11/1985 | White |
| 4,750,901 A | 6/1988 | Molteno |
| 4,862,891 A | 9/1989 | Smith |
| 4,936,825 A | 6/1990 | Ungerleider |

(Continued)

FOREIGN PATENT DOCUMENTS

| EP | 0858788 | 8/1998 |
| JP | 2001-504732 | 4/2001 |
| WO | WO98/23237 | 6/1998 |
| WO | WO02/36052 | 5/2002 |

OTHER PUBLICATIONS

International Search Report dated Apr. 23, 2008 for corresponding European Patent Application No. 03755839.2 [ISSCP003EP].
Jocson, VL, "Air Trabeculotomy", *American Journal of Ophthalmology*, vol. 79, No. 1, pp. 107-111, Jan. 1975.

(Continued)

*Primary Examiner*—Vy Q Bui
(74) *Attorney, Agent, or Firm*—Weaver Austin Villeneuve & Sampson LLP

(57) ABSTRACT

The invention provides minimally invasive microsurgical tools and methods to form an aqueous humor shunt or bypass for the treatment of glaucoma. The invention enables surgical creation of a tissue tract (7) within the tissues of the eye to directly connect a source of aqueous humor such as the anterior chamber (1), to an ocular vein (4). The tissue tract (7) from the vein (4) may be connected to any source of aqueous humor, including the anterior chamber (1), an aqueous collector channel, Schlemm's canal (2), or a drainage bleb. Since the aqueous humor passes directly into the venous system, the normal drainage process for aqueous humor is restored. Furthermore, the invention discloses devices and materials that can be implanted in the tissue tract to maintain the tissue space and fluid flow.

9 Claims, 5 Drawing Sheets

U.S. PATENT DOCUMENTS

| | | |
|---|---|---|
| 5,071,408 A | 12/1991 | Ahmed |
| 5,178,604 A | 1/1993 | Baerveldt et al. |
| 5,180,362 A | 1/1993 | Worst |
| 5,300,020 A | 4/1994 | L'Esperance, Jr. |
| 5,338,291 A | 8/1994 | Speckman et al. |
| 5,370,607 A | 12/1994 | Memmen |
| 5,372,577 A | 12/1994 | Ungerleider |
| 5,397,300 A | 3/1995 | Baerveldt et al. |
| 5,411,473 A | 5/1995 | Ahmed |
| 5,558,629 A | 9/1996 | Baerveldt et al. |
| 5,616,118 A | 4/1997 | Ahmed |
| 5,681,275 A | 10/1997 | Ahmed |
| 5,785,674 A | 7/1998 | Mateen |
| 5,807,302 A | 9/1998 | Wandel |
| 5,882,327 A | 3/1999 | Jacob |
| 5,891,084 A * | 4/1999 | Lee ............................ 604/521 |
| 6,050,970 A | 4/2000 | Baerveldt |
| 6,056,700 A | 5/2000 | Burney et al. |
| 6,261,256 B1 | 7/2001 | Ahmed |
| 6,450,984 B1 | 9/2002 | Lynch et al. |
| 6,471,666 B1 | 10/2002 | Odrich |
| 6,508,779 B1 | 1/2003 | Suson |
| 6,533,768 B1 | 3/2003 | Hill |
| 6,595,945 B2 | 7/2003 | Brown |
| 6,666,841 B2 | 12/2003 | Gharib et al. |
| 2002/0013546 A1 | 1/2002 | Grieshaber et al. |
| 2002/0026200 A1 | 2/2002 | Savage |

OTHER PUBLICATIONS

Office Action dated Jun. 2, 2009 for corresponding Japanese Application No. 2004-538229. [ISSCP003JP].

* cited by examiner

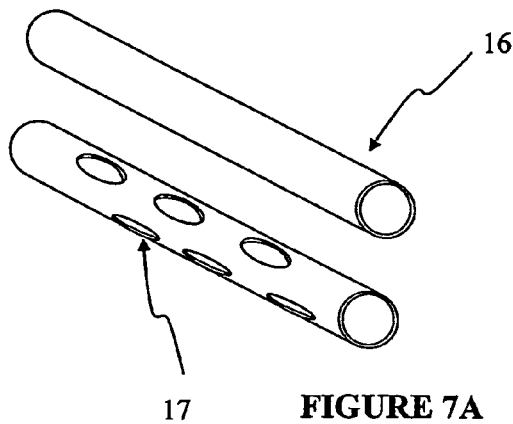
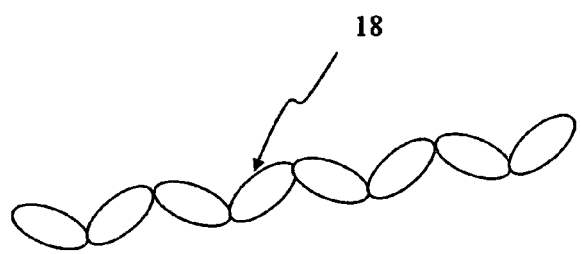
17  FIGURE 7A  FIGURE 7B
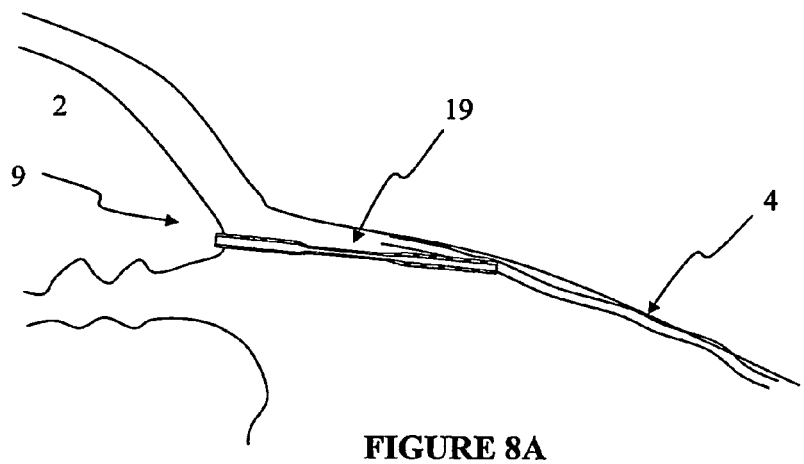
FIGURE 8A
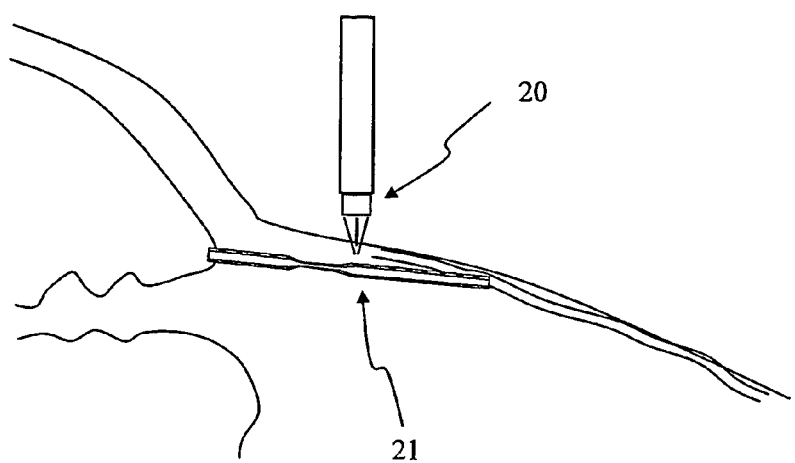
FIGURE 8B

APPARATUS AND METHOD FOR SURGICAL BYPASS OF AQUEOUS HUMOR

CROSS-REFERENCE TO RELATED APPLICATION

This application is related to and priority claimed from International Application No. PCT/US2003/029488 filed on Sep. 17, 2003, which claims priority of U.S. Provisional Patent Application No. 60/411,668, filed on Sep. 17, 2002, which is hereby incorporated by reference.

BACKGROUND OF THE INVENTION

Glaucoma is a disease condition of the eye in which increased intraocular pressure (IOP) is created by dysfunction in the drainage mechanism for the aqueous humor. Aqueous humor is produced within the eye in the ciliary body and flows within the anterior region of the eye. The aqueous humor normally flows through a network of tissues at the interior angle of the anterior chamber, named the trabecular meshwork and subsequently into a circular drainage space named Schlemm's canal. The aqueous humor continues its drainage path into collector channels and finally into aqueous veins to enter the venous system.

Typically in open angle glaucoma, the pathway for aqueous humor becomes narrowed or occluded, increasing IOP and resulting in gradual nerve damage and loss of vision. Such conditions are usually treated by topical drugs in the form of eye drops, but may result in surgical treatment if drug treatment becomes ineffective or if patient compliance is an issue. Traditional glaucoma surgery, such as trabeculotomy or trabeculectomy, involves dissection of the eye and the forming of new holes through the trabecular meshwork portion of the drainage pathway. The fluid is channeled to a reservoir formed under the conjunctiva known as a bleb. While blebs are effective in removing the aqueous humor, bleb complications present the highest incidence of post-surgical complications due to irritation and infection.

A new class of surgical procedures aims to approach treatment of the ocular drainage system from the scleral tissues without penetrating the interior chamber of the eye. These procedures are termed "non-penetrating" surgery and involve careful surgical dissection of the scleral tissues to access the tissues involved with ocular drainage. Deep sclerectomy is a form of this type of procedure in which a portion of intrascleral tissue is removed nearly to Descemet's membrane to allow significant aqueous flow from the anterior chamber to a bleb. Viscocanalostomy is another non-penetrating procedure, which increases the flow of aqueous humor form the anterior chamber into a surgically created intrascleral lake. Although non-penetrating procedures present fewer direct complications than traditional surgeries, most of the procedures still require the surgical dissection of ocular tissues and a high level of surgical skill.

Various approaches and devices for glaucoma surgery involving the rerouting of aqueous humor have been described in the art. One approach involves the shunting of aqueous humor through a tube in the anterior chamber into a reservoir implanted on the surface of the eye. See Mendez U.S. Pat. No. 4,428,746, White U.S. Pat. No. 4,554,918, Molteno U.S. Pat. No. 4,750,901, Ahmed U.S. Pat. No. 5,071,408, U.S. Pat. No. 5,411,473, U.S. Pat. No. 5,616,118, U.S. Pat. No. 5,681,275, U.S. Pat. No. 5,785,674, U.S. Pat. No. 6,261,256, Baerveldt, et al. U.S. Pat. No. 5,178,604, U.S. Pat. Nos. 5,397,300, 5,558,629, 6,050,970, Speckman U.S. Pat. No. 5,338,291, Memmen U.S. Pat. No. 5,370,607, Jacob U.S. Pat. No. 5,882,327, Odrich U.S. Pat. No. 6,41,666. A similar approach is to shunt the aqueous humor through a tube placed in the anterior chamber into a bleb on the surface of the eye. See Worst U.S. Pat. No. 5,180,362, Suson U.S. Pat. No. 6,508,779, Wilcox WO 02/32343.

Another approach described in the art is the shunting of aqueous humor from the anterior chamber to the tear film of the eye. See Ungerleider U.S. Pat. No. 4,936,825; U.S. Pat. No. 5,372,577; Wandel U.S. Pat. No. 5,807,302; Brown U.S. Pat. No. 6,595,945.

Another approach described in the art is placing a shunt for aqueous humor through the trabecular meshwork to connect the anterior chamber and Schlemm's canal. See Lynch et al. U.S. Pat. No. 6,450,984, Hill U.S. Pat. No. 6,533,768, WO 01/78656, and Gharib et al. U.S. 2002 0165478.

SUMMARY OF THE INVENTION

The invention provides an apparatus for creating a tract within the scleral tissues of an eye comprising an elongated body portion shaped to create a tract which forms a path for flow of aqueous humor into an ocular vein. The elongated body portion has a proximal end and a distal end. The distal end may comprise a mechanically cutting tip or an energy source to ablate tissue. The distal end may be visible by medical imaging methods such as ultra sound, or optical coherence topography or visible under direct observation by an optical beacon at the tip. The apparatus may additionally accommodate a space-maintaining material for placement within the tract, such as hyaluronic acid or a cell proliferation inhibitor. These space-maintaining materials may also comprise a stent device made of hyaluronic acid, nickel, titanium alloy or other material.

The invention also provides a method for creating a path for flow of aqueous humor of the eye into an ocular vein comprising;

a. inserting an apparatus to form a tissue opening into an ocular vein on the anterior portion of the eye;

b. directing the apparatus to create a tract from the vein to a source of aqueous humor, c. removing the apparatus;

d. closing the tissue opening while retaining flow through the tract between the vein and the source.

In another embodiment of the method the path is created by a. inserting the apparatus through a tissue opening in the eye into a source of aqueous humor;

b. directing the apparatus to create a tract from the source into an ocular vein;

c. removing the apparatus while retaining flow through the tract between the vein and the source; and d. optionally closing the tissue opening.

The source of aqueous humor typically will comprise the anterior chamber, Schlemm's canal, the collector channel or a bleb.

BRIEF DESCRIPTION OF THE DRAWINGS

FIG. 7A. View of an embodiment of the invention comprising tube-stent devices.

FIG. 7B. View of a stent device comprising alternating filament loops.

FIG. 8A. Sectional view of the anterior portion of the human eye showing bypass implant comprising shape memory material incorporating a reduced diameter segment to maintain flow control at a minimum level.

FIG. 8B. Sectional view of the anterior portion of the human eye showing laser energy being applied externally to increase the diameter of the shape memory bypass implant.

DESCRIPTION OF INVENTION

The present invention to provide minimally invasive microsurgical tools and methods, which enable surgical creation of a tissue tract within the tissues of the eye to directly connect a source of aqueous humor such as the anterior chamber, to an ocular vein, thereby forming a shunt or bypass for aqueous humor. The aqueous veins, into which aqueous humor normally drains, are good candidates for this procedure, however the invention is not limited to these specific vessels. Furthermore, the tissue tract from the vein may be connected to any source of aqueous humor, including the anterior chamber, an aqueous collector channel, Schlemm's canal, or a drainage bleb. Since the aqueous humor passes directly into the venous system, the normal drainage process for aqueous humor is restored. The tools and methods effectively bypass the small anatomical structures of the drainage system, such as the trabecular meshwork, Schlemm's canal and the collector channels, which have been identified with the mechanism of glaucoma. Furthermore, the invention describes devices and materials that can be implanted in the tract to maintain the tissue space and fluid flow post operatively.

Figure 1:
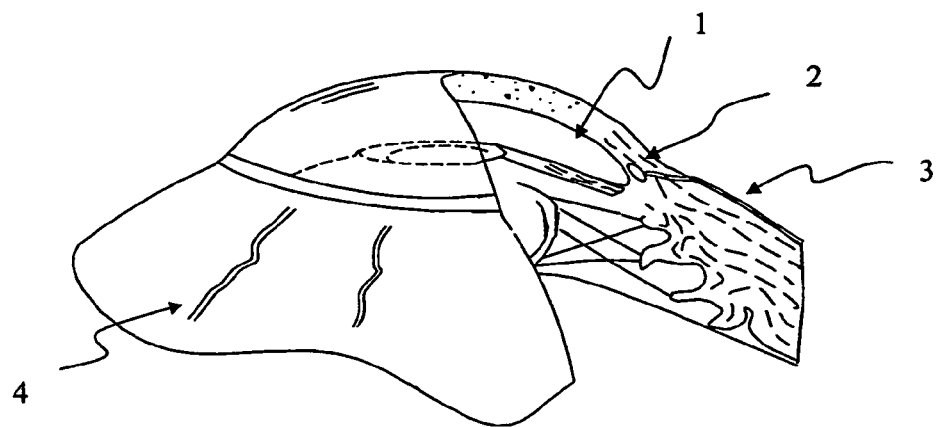
FIG. 1. Sectional view of the anterior portion of the human eye.

The invention comprises tools, materials and related methods to surgically create a bypass for aqueous humor. FIG. 1 shows a sectional view of the anterior portion of the human eye for reference. The invention involves the steps of: firstly, identifying a candidate vein 4 on or within the eye of a living subject; secondly, inserting one or more tools into the eye to create a tissue tract in the sclera 3, that connects the vein to a source of aqueous humor such as the anterior chamber of the eye 1, or Schlemm's canal 2; thirdly, optionally inserting an implant or material to maintain the tract opening and fluid flow, and; lastly, closing the surgical access site as required. The tools and materials comprise the apparatus to create a tissue tract within scleral tissues of the eye such that the tract acts as a fluid path for aqueous humor to the vein.

Figure 2:
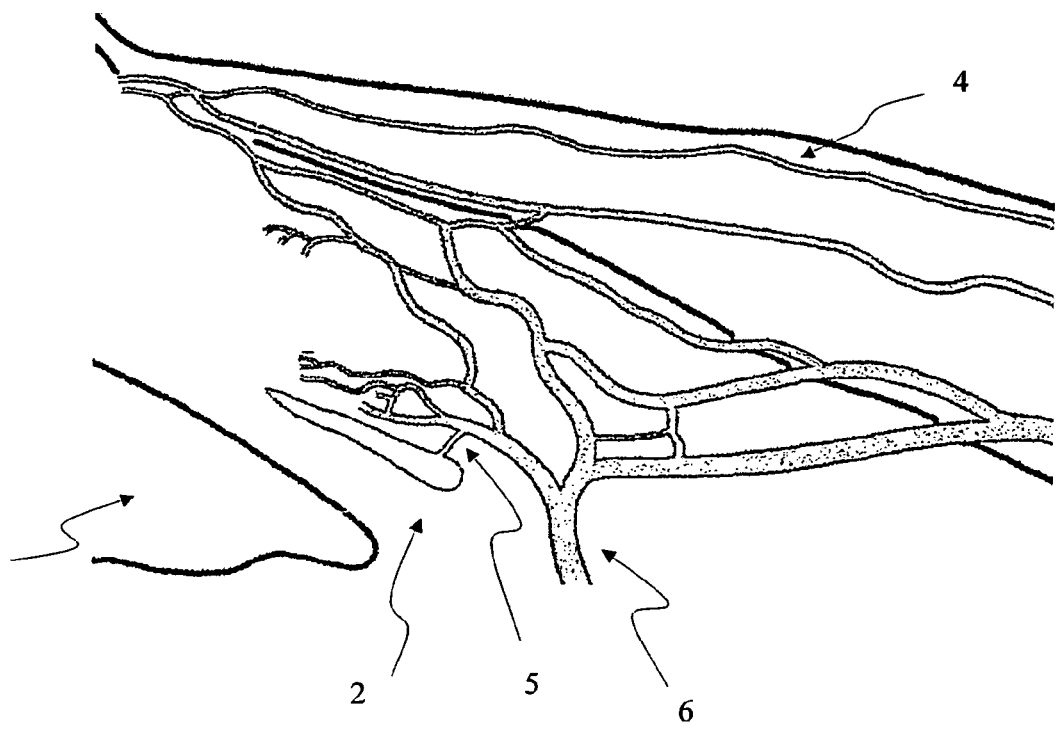
FIG. 2. Cross-sectional view of the drainage system in the human eye.

A magnified cross-sectional view of the drainage system of the human eye is shown in FIG. 2 for reference. An episcleral vein 4 is identified suitable for creating the bypass. Candidate vessels can be found close to the surface of the eye, such as but not limited to, conjunctiva veins, anterior ciliary veins, and episcleral veins. Surface vessels can be directly visualized and accessed while subconjunctival vessels may require a small incision in the conjunctiva for access. Subsurface vessels such as collector channels 5 and aqueous veins 6 can be identified by high-resolution medical imaging methods such as high frequency ultrasound (HFU) or optical coherence topography (OCT). The use of medical imaging is preferred in that veins which are in the most surgically desired location, can be selected. Vessels which are angled toward the anterior chamber 1, or Schlemm's canal 2, and having appropriate dimensions and minimal tortuosity, can be identified as candidates for bypass. The use of an ultrasound or optical contrast agent, either delivered directly to the candidate vein or systemically to the subject, will facilitate vein identification. Doppler imaging can be used to assist identification of candidate blood vessels. Pressure changes applied to the anterior chamber will also facilitate vein identification and selection by distinguishing vessels with the most direct connection to the aqueous drainage system. In some situations the blood/aqueous interface can be seen in episcleral veins. Changes in pressure in the chamber will cause this interface to move forward and backward within the vein. Furthermore, pressure changes can result in a change of the apparent vein diameter, which can be directly observed.

Figure 3:
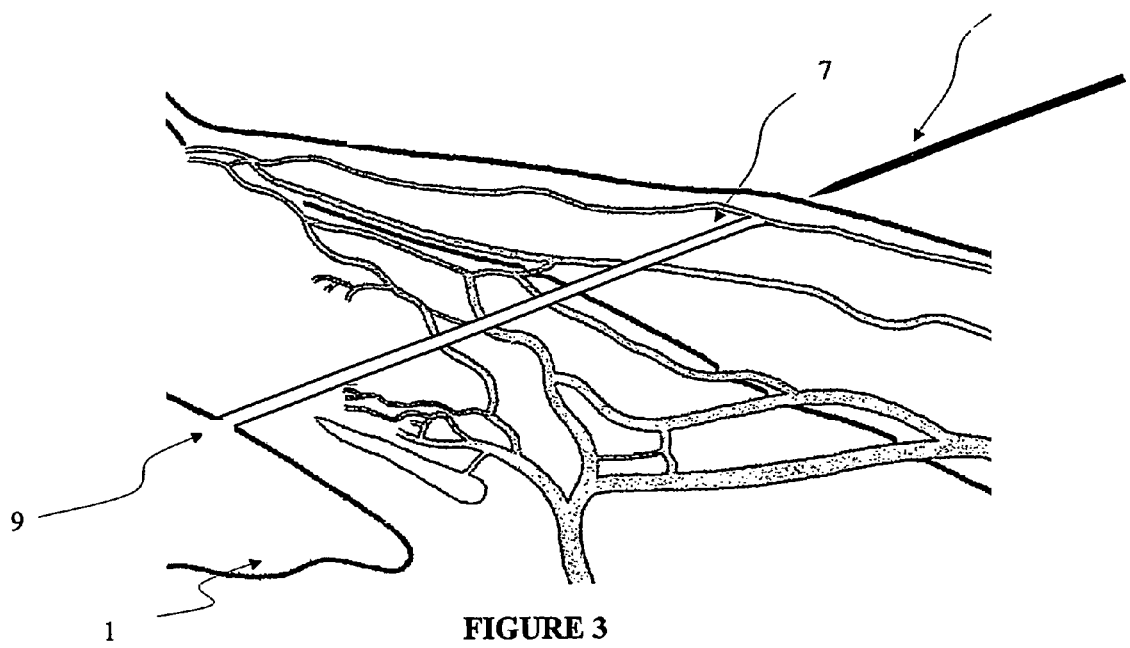
FIG. 3. Cross-sectional view of the drainage system in the human eye showing a microsurgical tool and tissue tract from an episcleral vein to the anterior chamber.
Figure 4:
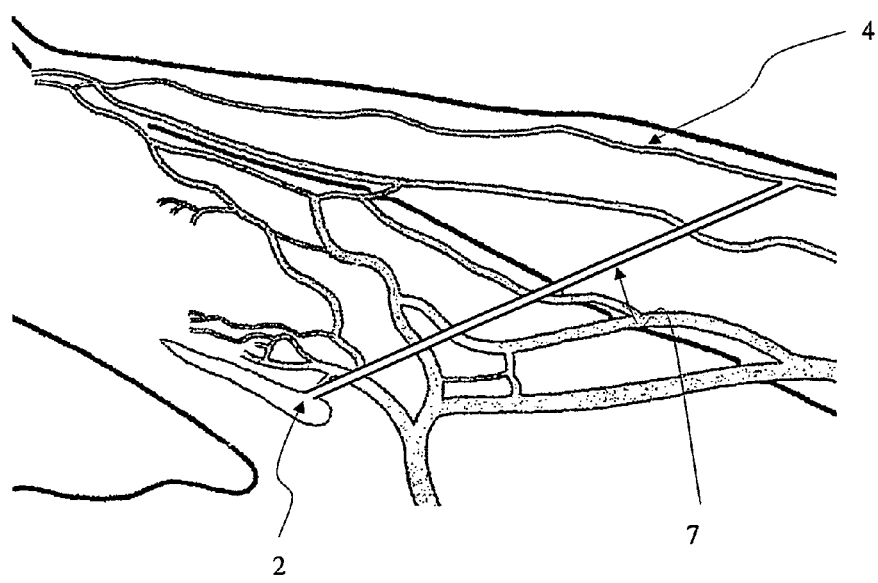
FIG. 4. Cross-sectional view of the drainage system in the human eye showing tissue tract from an episcleral vein to Schlemm's canal.

Cross-sectional views of the drainage system of the human eye with a surgically created tissue tract are shown in FIGS. 3 and 4 for reference. The use of HFU or OCT imaging is desired to determine the optimal placement of the tissue tract 7, from the candidate vein to the anterior chamber 1, or if desired, to a collector channel, Schlemm's canal 2, or an existing bleb. When forming a connection 9 of a vein to the anterior chamber, any region of the anterior chamber in proximity to the vein may be used including the area at the anterior segment angle and the corneal-scleral junction. The surgeon may use imaging techniques to pre-plan the route of the surgery and to verify locations, direction and placement of the microsurgical tool 8, during the procedure. The method may comprise first access to a vein 4, and then creating a tract 7, toward and into a source of aqueous humor such as the anterior chamber 1. Alternatively, the method may comprise access from the anterior chamber first, and then through the subsurface tissues to a vein. The advantage of such a method is that the tissue penetration may be accomplished through clear cornea, starting 180° from the bypass point and transversing through the anterior chamber. The microsurgical tool is placed at the correct site for penetration of the tissues through to the candidate vein. Small, clear corneal incisions are self-sealing and therefore do not require closure mechanisms. If the initial penetration of the tool into the eye is elsewhere, then the entry incision may need to be closed after removal of the tool.

Figure 5:
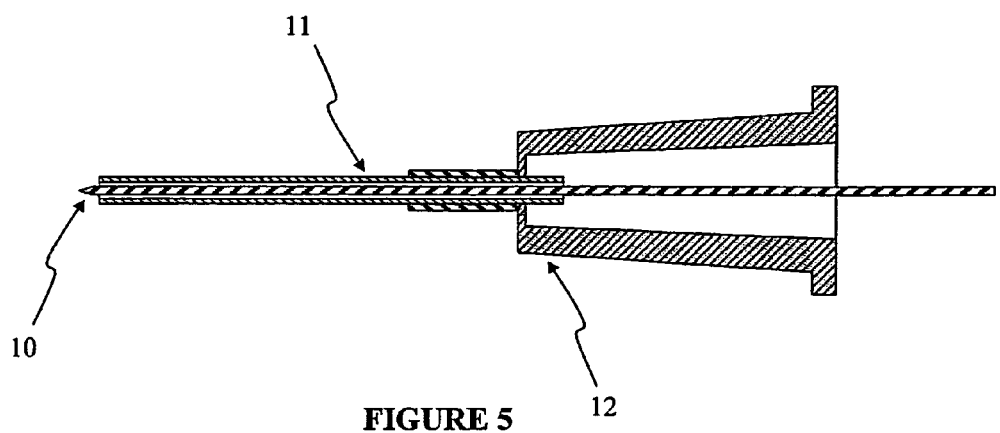
FIG. 5. Cross-sectional view of the of an embodiment of the invention comprising a microcannula assembly.

The microsurgical tool may comprise an elongated tool, such as a microcannula, with a tip at one end which is directed into a vein. This may be a mechanically cutting tip such as a solid or hollow trocar-like member capable of creating a tunneled tract of controlled diameter through scleral tissues. In another embodiment, the tool may comprise a hollow tube with a sharpened distal edge used to core out a tissue tract. The removal of tissue may promote the subsequent stability of the tract and aid placement of an implant device into the channel. Referring to FIG. 5, the tool may comprise an outer sheath 11 and inner member, with the outer sheath disposed axially about the inner member. The inner member may comprise a trocar 10, solid rod, hollow rod or cylinder, needle, wire or optical fiber. The inner member may be designed to allow exchange during use to allow specific functions to be brought to the tip of the tool once it is located in tissue. The microcannula may be handled at its proximal end by a suitable accommodating mechanism such as luer fitting 12.

Figure 6:
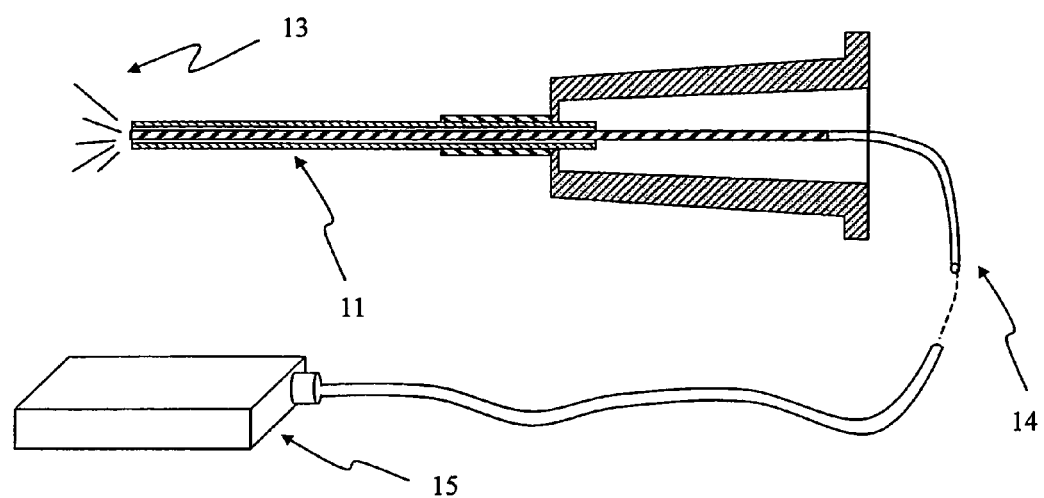
FIG. 6. View of an embodiment of a microcannula assembly incorporating fiber optic core for transmission of energy from a source.

Referring to FIG. 6, an optical fiber inner member may be used to carry visible light to the tip of the fiber 13, which may be disposed to reside at the tip of the sheath and hence may be used for direct visualization of the location of the tool through scleral tissues. In the case of an opaque outer sheath material, a cutout section or window near the distal tip of the sheath may be provided to visualize the optical fiber tip. The optical fiber may be fabricated from glass, fused silica, or plastic that is optically transparent to the wavelength of light used for visualization. The described optical beacon can provide an adjunct method of tracking the creation of the tract, aiding HFU or OCT imaging. Alternately, the optical fiber may be used to carry energy for tissue ablation such as laser energy, in order to create the tract. The tip may also accommodate transmission of radio frequency or thermal energy to ablate or coagulate tissue. The fiber optic line 14 is connected to energy source 15.

The microsurgical tool is sized appropriate for access through small vessels and to create controlled diameter tissue tracts. Diameters from 50-500 microns are useful, and in particular diameters from 50-200 microns are preferred. Outer diameter of a sheath member may correspond to these ranges and may comprise a wall thickness between 10 and 100 microns. The microsurgical tool can comprise a flexible microcannula to allow the distal tip to be advanced within the vein toward a source of aqueous humor such as the anterior chamber. The microsurgical tool may be fabricated from structural materials such as metals including steel, titanium, and nickel-titanium alloys, structural polymers including polyimide, polyethylene, polyamide, polypropylene, polystyrene, polymethylmethacrylate, polytetrafluoroethylene, and polysulfone. Several tools with different material composition and design may be used sequentially in the surgical procedure. For example, one tool may be used to access the vessel and exchanged with a tool to create the scleral tissue tract. Alternatively, different types of inner members such as for cutting or light conduction may be used interchangeably within an outer sheath.

The tool will accommodate features for orientation of the tract identified and controlled by the clinical practitioner. The use of medical imaging to coordinate or verify the position and orientation of the tract aids accuracy and precision of tract placement. Tools which are in the field of view of the imaging system allow for identification of the tool's position while minimizing the creation of artifacts into the image. Selection of tool material and/or the use of contrast markers can provide the desired imaging properties for the tools.

The tract created may optionally be filled with a material to help maintain the patency and fluid flow of the tract. Such materials may comprise an anti-fibrotic material, anti-thrombotic agent, space maintaining material, tube-like stent or similar device to assure that the drainage tract remains patent. Anti-fibrotic materials such as hyaluronic acid and cellular proliferation inhibitors such as methotrexate, sirolimus, and paclitaxel, may be applied or released from a device within the tract. Anti-thrombotic agents such as heparin and tissue plasminogen activator may also be applied or released from a device within the tract. Such materials may be in the form of microspheres, microparticles, microfibers, open- or closed-cell matrices, foams, gels and tubes, which may be designed to change their configuration in-situ after implantation. The materials may comprise degradable materials such as hyaluronic acid, collagen, glycosoaminoglycans and degradable synthetic polymers. The materials may also comprise non-degradable materials with biocompatibility suitable for implant use including metals such as steel, titanium, and nickel-titanium alloys, and polymers such as polytetrafluoroethylene, polymethylmethacrylate, polyimide, polyethylene, polypropylene and polysulfone.

Figure 9:
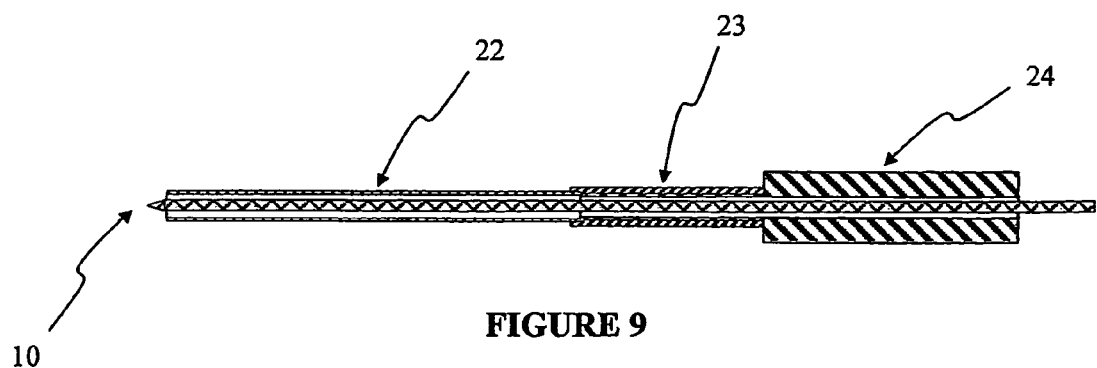
FIG. 9. Cross-sectional view of microcannula assembly incorporating a detachable tube stent as the distal sheath of the assembly.

A tubular stent-like device may be placed within the tract to enlarge the tract diameter or provide stabilization through mechanical means. Referring to FIG. 7a, there are examples shown of a simple tube 16 and a fenestrated tube 17. The outer sheath of the microsurgical tool may comprise a tube-stent, and can be left behind after the tool core is removed. Referring to FIG. 9, there is shown such a microcannula assembly comprising a trocar tip core 10, the detachable stent 22, driving cannula 23, and handle 24. The tube-stent may be pre-sized based on pre-surgical imaging or may be designed to be cut to size prior to or after implantation. The venous end of the tube-stent may be implanted to reside in the vein or further advanced to reside in a collector channel. The tube-stent may reside in the entire tissue tract between the vein and the aqueous humor source, or a portion of the tract. Several discrete tube-stents may also be used in stabilizing the tissue tract.

The diameter of the tube-stent may be designed to allow expansion in-situ, for example, by hydraulic pressure or thermal energy, or through the use of shape memory materials for construction of the tube-stent. Referring to FIG. 8b, a laser 20 is used to increase the diameter of a shape memory implant 21. For long-term stability, preferred are tube-stents designed to be conformable to the tissue tract and that do not create mechanical loads on the tissue other than for dilation of the tract. Mechanical features of the tube-stent such as tissue interfacing porosity may be incorporated to aid retention. Tube-like stents may be comprised of permanent or biodegradable materials. Suitable materials include metals such as steel, titanium and nickel titanium alloys, and biocompatible polymers such as hyaluronic acid, collagen, glycosoaminoglycans, polylactic acid, polyglycolic acid, polytetrafluoroethylene, polymethylmethacrylate, polyimide, polyethylene, polypropylene and polysulfone Furthermore, the tube-stent device can also have a design to provide a controlled amount of flow restriction that would limit retrograde flow of blood. Devices with different flow resistance may be fabricated and chosen for optimization of aqueous flow by the practitioner. Referring to FIG. 8a, a shape memory stent incorporating a reduced diameter segment 19 connects the anterior chamber 2 with an episcleral vein 4 via entry point 9. A valve may be incorporated into the tube stent to limit retrograde flow or to set a threshold pressure for flow. In another embodiment, the flow characteristics of the tube-stent may be varied after the procedure upon examination of the patient's IOP. Various energy sources such as laser light, RF or microwave may be directed at a portion of the implant to dilate or contract discrete segments to control flow. A photoreactive polymer or a pre-stressed polymer similar to heat shrink tubing may be employed to perform this function.

In a similar embodiment, the stent-like device may comprise a series of filaments or wires. Referring to FIG. 7a, the device may be formed as a woven tube or a series of filament loops 18. The filament loops may be attached to each other in an alternating, or "zig zag" pattern, or may be attached to a linear member along one axis. The loops may be disposed at an angle to the axis, and be sufficiently flexible to maintain the tract opening without creating undue stress upon the surrounding tissues. Such an embodiment allows for the stent device to conform to changes in diameter or direction of the tract.

Figure 10A:
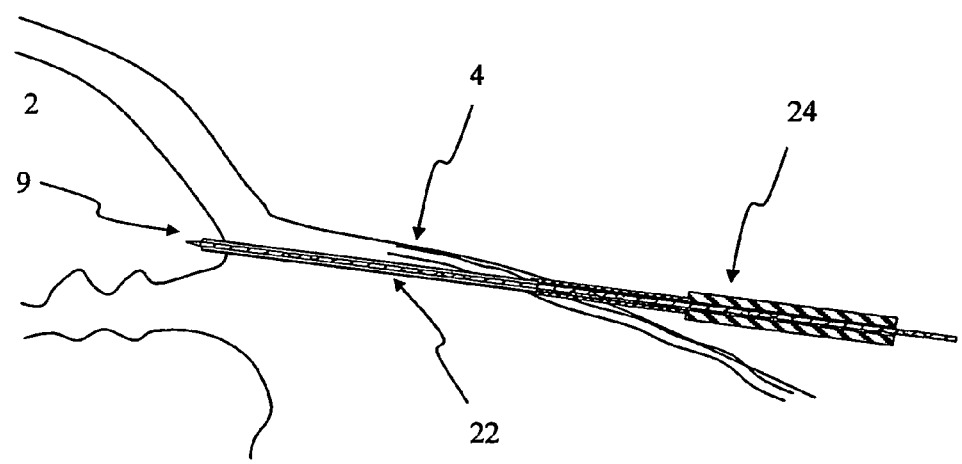
FIG. 10A. Sectional view of the anterior portion of the human eye showing detachable tube stent assembly creating tract from an episcleral vein to the anterior chamber.
Figure 10B:
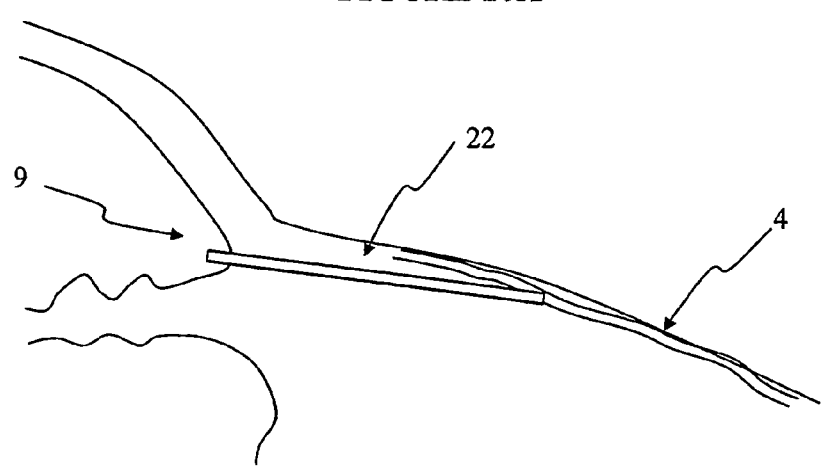
FIG. 10B. Sectional view of the anterior portion of the human eye showing tube stent in place after removal of the cannula assembly.

The invention also provides methods to surgically create an aqueous bypass in the eye. The following methods are provided as explanatory and do not constitute the entire scope of methods which may be used in conjunction with the microsurgical tools described herein. Referring to FIGS. 10a and 10b, in a first example, the surgeon will visually identify a candidate vein 4 on or about the surface of the eye. Using high resolution imaging techniques, a pathway from a target point along the axis of the vein to the desired endpoint, such as the anterior chamber 2, is mapped. A surgical tool comprising a handle 24, tube stent sheath 22, and trocar is used. The trocar has a distal point configured to pierce the tissues. The tube-stent will be of correct length to connect the chamber and vein. The vein is cannulated with the tool at the target point, and the tool oriented in the angle and direction that was plotted from the imaging session. The tool is advanced along the pathway until the tip is seen penetrating the anterior chamber at entry point 9, preferably above the iris. The trocar inner member and the tool are removed, leaving the tube-stent 22 behind. Alternatively, a syringe containing an antifibrotic hydrogel can be attached to the proximal end of the sheath. The hydrogel is applied into the tract at the same time that the tool, including the sheath, is being withdrawn, to aid in maintaining the tract. The access site is then sealed by any requisite surgical method.

In another example, an episcleral vein is located by visualization through a surgical microscope. A target point is designated along the vein, at a distal point of sufficient diameter to accept the incoming microsurgical tool. An entry point is determined along the corneal limbus approximately 180° away from the candidate vein. A gonio lens is used to visually inspect the anterior angle at the bypass site to choose a target entry point to connect to the vein. The microsurgical tool in this instance comprises a fiber optic inner member with a trocar like distal tip and an outer member comprising a tube-stent of the correct length to connect the chamber and vein. The tool is advanced through the clear cornea at the entry point and advanced across the anterior chamber to the tissue entry point. The tool is then advanced through the tissues guided toward the candidate vein by visualization of the beacon tip of the tool. The tool is advanced until the distal tip enters the vein and then continued until a sufficient portion of the tube stent distal end is within the vessel to maintain flow. If sized correctly, the proximal end of the tube stent will now reside just within the anterior chamber. The tool is withdrawn, leaving the tube stent behind. The entry point may be surgically closed or allowed to self-seal.

The procedure may also be performed on more than one venous site per eye as may be required to provide adequate drainage. In practice, the procedure may be performed on one site, and the patient's IOP monitored post-surgically. If more pressure reduction is required, then a subsequent procedure may be performed at another target site. Multiple drainage paths can thereby be created.

What is claimed is:

1. A method for creating a path for flow of aqueous humor of the eye into an ocular vein comprising:
    a) inserting an apparatus having a proximal end and distal end, said distal end comprising a beacon tip for visualizing said apparatus for guidance to form a tissue opening into an ocular vein on the anterior portion of the eye;
    b) directing said apparatus by visualization of said distal tip to create a tract from said vein to a source of aqueous humor;
    c) removing said apparatus;
    d) closing said tissue opening while retaining flow through said tract between said vein and said source.

2. A method for creating a path for flow of aqueous humor of the eye into an ocular vein comprising:
    a) inserting an apparatus having a proximal end and distal end, said distal end comprising a beacon tip for visualizing said apparatus for guidance through a tissue opening in the eye into a source of aqueous humor in the eye;
    b) directing said apparatus by visualization of said distal tip to create a tract for said source into an ocular vein;
    c) removing said apparatus while retaining flow through said tract between said vein and said source.

3. A method according to claim 2 further comprising the step (d) of closing said tissue opening.

4. The method of claim 1 and 2 wherein said source of aqueous humor comprises the anterior chamber, Schlemm's canal, collector channel, or bleb.

5. The method of claim 1 or 2 wherein in said step (b) medical imaging is used to direct the creation of said tract.

6. The method of claim 1 or 2, which additionally comprises the step of placing a space maintaining material within said tract.

7. The method of claim 6 wherein said material comprises hyaluronic acid.

8. The method of claim 6 wherein said material comprises a stent device comprising a nickel titanium alloy.

9. The method of claim 8 wherein said material comprises a filament.

* * * * *